United States Patent [19]
Könst et al.

[11] 4,246,292
[45] Jan. 20, 1981

[54] SUBSTITUTED CYCLOHEXANONES AS FLAVOR MATERIALS

[75] Inventors: Wilhelmus M. B. Könst, Naarden; Roelof ter Heide, Bussum; Hendrik J. Wobben, Naarden, all of Netherlands

[73] Assignee: Naarden International N.V., Naarden-Bussum, Netherlands

[21] Appl. No.: 853,907

[22] Filed: Nov. 22, 1977

[30] Foreign Application Priority Data

Nov. 23, 1976 [GB] United Kingdom ............... 48762/76

[51] Int. Cl.³ ............................................. A23L 1/235
[52] U.S. Cl. ................................... 426/538; 568/376; 252/522 R; 131/17 R; 568/377
[58] Field of Search ...................... 426/538; 131/17 R; 260/586 R

[56] References Cited

U.S. PATENT DOCUMENTS

| 3,268,589 | 8/1966 | Rowland | 260/586 R |
| 3,746,010 | 7/1973 | Leffingwell | 131/17 R |
| 3,881,025 | 4/1975 | Flament | 260/586 R X |
| 3,927,107 | 12/1975 | Schulte-Elte et al. | 426/538 X |
| 4,076,854 | 2/1978 | Light et al. | 426/538 |
| 4,084,009 | 4/1978 | Light et al. | 426/538 |

Primary Examiner—Joseph M. Golian
Attorney, Agent, or Firm—Brumbaugh, Graves, Donohue & Raymond

[57] ABSTRACT

This invention relates to novel chemical compounds and their use as flavor and odor agents. More specifically this invention relates to substituted cyclohexenones and cyclohexanones, which are valuable flavor and fragrance materials.

8 Claims, 1 Drawing Figure

1.
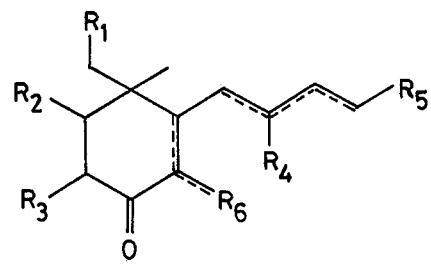
Reaction scheme A
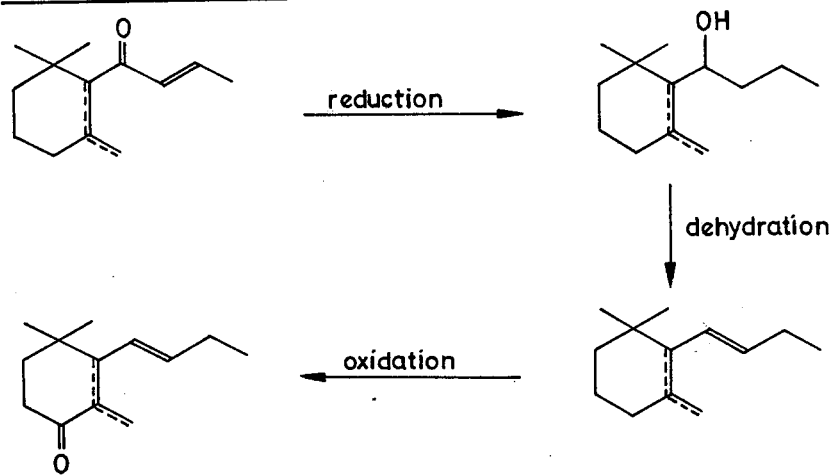
Reaction scheme B
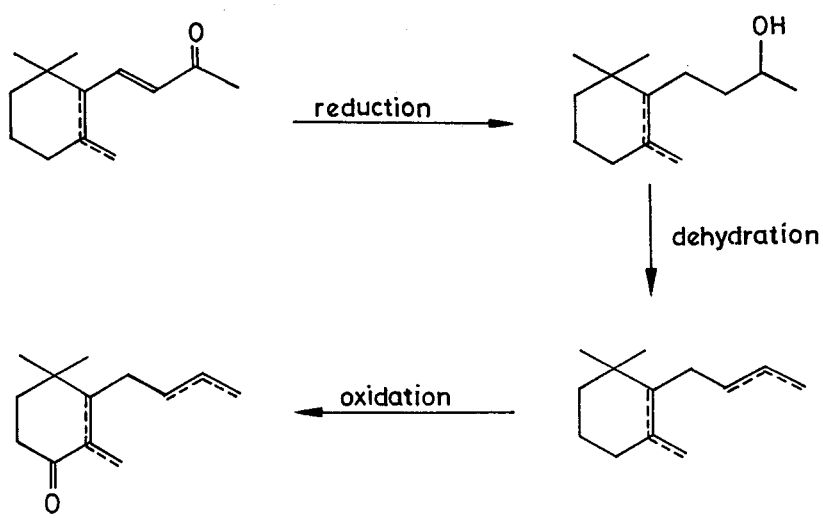

SUBSTITUTED CYCLOHEXANONES AS FLAVOR MATERIALS

Increasing attention is being paid to the preparation and use of artificial fragrance and artificial flavour compounds in foodstuffs, beverages, pharmaceuticals, tobacco, petfood, etc. This attention has been stimulated not only because of the inadequate quantity of natural flavour and fragrance materials, but perhaps even more importantly because of the need for materials which can combine several nuances, will blend better in perfume and flavour compositions and will give perfumed and flavoured products, which can be specifically tailored to a given use. Moreover these artificial flavour and fragrance compounds can be duplicated at will, which confers a major advantage over natural products, such as essential oils, extracts, concentrates and the like, since natural products are always subject to wide variations in quality.

This invention deals with substituted cyclohexenones and cyclohexanones with a structure according to the general formula 1, shown in the accompanying formulae drawings, wherein $R_1$, $R_2$, $R_3$, $R_4$ and $R_5$ may be the same or different and are H or methyl groups, the dotted lines indicate possible double bonds, provided that the side chain carrying $R_4$ and $R_5$ contains not more than one double bond, and $R_6$ means hydrogen or a methyl or ethyl group when no double bond to $R_6$ is present, or a methylene or ethylidene group when a double bond to $R_6$ is present. Several alkyl substituted cyclohexenones are known to be useful as flavour or fragrance compounds. However these compounds either differ in the positions of the geminal dimethyl group and the long alkyl side chain relative to the keto group, or they contain an extra functional group in the side chain. Thus: 3,5,5-trimethyl-4-butenyl-cyclohex-2-en-1-ene and several double bond isomers are described in French Pat. No. 1,533,234. On the other hand 2,4,4-trimethyl-3(2'-oxo-but-3'-en-4'-yl)-cyclohex-2-en-1-one as well as the corresponding side chain alcohol are described in U.S. Pat. No. 3,746,010, and the corresponding 1'-oxo-but-2'-en-1'-yl substituted compound and some homologues are described in the German Offenlegeschrift (DOS) No. 2,353,468.

The compounds French Pat. No. 1,533,234 and U.S. Pat. No. 3,746,010 are described as having a strong tobacco-like aroma, whereas the compounds of DOS No. 2,353,468 are quoted to have especially sweet fruity aroma notes.

The compounds of this invention have not been described before and are structurally very different from the compounds of the above cited prior art. They lack the side chain functional group of the compounds of U.S. Pat. No. 3,746,010 and DOS No. 2,353,468 on one hand and have the keto group and the ring double bond in a different position compared with the compounds of French patent No. 1,533,234 on the other hand.

We found that the new substituted cyclohexenones and cyclohexanones of this invention possess useful organoleptic properties. They have strong fruit-like odours and flavours with distinct woody and herbal notes. The fruit-like character is best described as reminding of raspberry. Some of the compounds of the invention also possess flowery notes, best described as rose-like. Some variations in odour and flavour strength and quality exist within the group of compounds of the invention as described above. Preferred as flavour and fragrance materials are those compounds wherein $R_1$ stands for hydrogen and wherein only one of R2, R3, R4 and R5 is methyl, the others being hydrogen. Especially preferred are the compounds wherein R2, R3, R4 and R5 are all hydrogen.

It will be apparent to the expert that several compounds comprised in this invention exist in a cis and trans form. These isomers may be separated, especially by column chromatography and GLC. In most cases the isomers slightly differ in organoleptic properties. However the mixture of isomers is perfectly suitable for most purposes, rendering a laborious separation procedure superfluous. The compounds of the invention may be used as such as aroma or fragrance materials, or they may first be combined with carriers or diluents. They may also be compounded with other single compounds or mixtures (e.g. essential oils) in a manner conventional in the art to form aroma or perfume compositions. The term aroma (perfume composition is used here to mean a mixture of flavour (odour) and auxiliary materials, dissolved in a suitable solvent or mixed with a suitable powdery substrate if desired, and used to impart a desirable flavour (odour) to various kinds of products, or strengthen the flavour (odour) they already have.

Examples of products to be flavoured are: foodstuffs, beverages including alcoholic drinks, tobacco, pharmaceuticals, etc. Products and articles to be perfumed are e.g. soaps, detergents, cleaners, room deodorants, cosmetic creams, ointments and other cosmetic products, etc.

The amounts of the compounds to be used according to the invention may vary widely and depends strongly on what product the flavour and fragrance compounds of this invention are used in. It also depends on the type and quantity of the other components in an aroma or perfume composition and on the desired type and strength of the aroma or perfume composition.

In most cases 0.005 ppm by weight of a compound according to this invention will already be clearly perceptible in foodstuffs and beverages, whereas quantities of up to 100 ppm may be used if the specific aroma of the compound should be the main aroma note in a foodstuff.

In concentrated perfume compositions quantities of only 0.05% by weight will generally have a clearly perceptible effect on the odour impression, but also quantities of up to 10% may be used for purposes requiring a strong odour impact. In products perfumed with compositions containing the compounds of this invention, the quantities of these compounds may be much lower, depending on the quantity of the composition that has been incorporated in the product. The compounds of this invention may be prepared according to the reaction sequences outlined in reaction scheme A and B of the formulae drawings. These reaction schemes are given for the specific case that $R_1=R_2=R_3=R_4=R_5=H$ and $R_6$ is methyl or methylene but apply also to the synthesis of the other compounds of this invention. Reaction scheme A starts with β or γ damascone or its homologues, whereas reaction scheme B starts with β or γ ionone, but also applies to the corresponding irones and methylionones and their homologues.

The preparation of β and γ damascone and their homologues is described in British Pat. Nos. 1,240,309 and 1,305,621 and in British Pat. No. 1,456,151, laid open to public inspection. Ionone homologues suitable as starting compounds in reaction scheme B may be prepared from citral homologues obtained according to British Patent No. 1,305,621 and literature cited therein.

The following examples illustrate the synthesis of the compounds according to the invention and the application of these compounds in flavouring and perfumery. However the examples are not intended to limit the invention thereto.

EXAMPLE 1

Synthesis of 2,4,4-trimethyl-3-(but-2'-en-1'-yl)-cyclohex-2-en-1-one and its (but-3'-en-1'-yl) isomer.

A solution of 192 g of β-ionone in 1 L of ethanol is subjected to catalytic hydrogenation at 10 ato and 100° C. using 2% Nickel catalyst. The catalyst is subsequently filtered off. The resulting dihydro-β-ionone is reduced in 4 hours at 5°–10° C. with 14 g NaBH₄ dissolved in ethanol. The resulting reaction mixture is acidified with acetic acid to pH 4. The solvent is distilled off under reduced pressure. 250 ml of water is added and the mixture is extracted 3 times with ether. The etheral solution is dried over Na₂SO₄ and the ether removed by evaporation. The residue is distilled under reduced pressure. B.p. 90° C./0.5 Torr; yield 85% (on β-ionone).

20 g of the resulting dihydro-β-ionol is dissolved in 65 ml of hexamethylphosphorous triamide and heated to reflux for one hour under a nitrogen atmosphere. The reaction mixture is cooled and a mixture of ice, saturated NaCl solution and pentane is added. The organic layer is separated and the water layer is extracted twice with pentane. The combined pentane layers are washed with water until neutral and dried over MgSO₄. The solvent is removed by evaporation. The residue is purified by column chromatography over silica, pentane is used as the eluent. Yield: 60%.

b 18 g (0.1 mole) of the resulting mixture of alkenes is dissolved in 18 ml of acetic acid anhydride and 150 ml of carbontetrachloride. A solution of 1 mole of tert-.butylchromate in 150 ml carbontetrachloride is added slowly at 40° C. The reaction mixture is subsequently refluxed for 6 hours. After cooling to room temperature, 10 ml of ethanol, 50 ml of acetic acid and 100 ml of water is added; the mixture is stirred well and filtered over hyflo. The organic layer of the filtrate is separated. The water layer is slightly acidified with acetic acid and extracted twice with carbontetrachloride. The combined organic layers are dried over MgSO₄ and solvent is removed by evaporation. The residue is distilled under reduced pressure. The fraction boiling between 120° and 140° C./13 Torr is collected and consists of a mixture of the title compounds (including cis and trans isomers of the but-2'-en-1-yl compound).

The compounds could be separated by gaschromatography over a 2 m column 10% DEGS at 175° C.

NMR spectral data: (δ in ppm relative to TMS; solvent CCl₄) but-2'-en-1'-yl isomer: (cis and trans).

1.14 (6H,s); 1.69 (3H,s); 2.9 (2H,m); 5.4 (2H,m) but-3'-en-1'-yl isomer:

1.17 (6H,s); 1.73 (3H,s); 4.8–6.1 (3H,m).

The cis-but-2'-en-1'-yl compound has a strong raspberry odour with a distinct woody and a less pronounced celery note. The trans compound has the same odour character although somewhat weaker.

The but-3'-en-1'-yl compound has a less pronounced raspberry odour but possesses a more flowery rose-like character.

EXAMPLE 2

The following compounds were prepared according to the procedure of example 1 (starting materials are also indicated):

2,4,4-trimethyl-3-(pent-3'-en-1'-yl)-cyclohex-2-en-1-one from n.methylionone (β).

NMR spectral data: (cis and trans isomer together): 1.17 (s) and 1.19 (s), (together 6H); 1.71 (m, 3H); 5.47 (m,2H).

The compound has a sweet fruity odour also reminding of vanillin, with distinct woody and cellery-like notes.

2,4,4,5-tetramethyl-3-(but-3'-en-1'-yl)-cyclohex-2-en-1-one and its (but-2'-en-1'-yl) isomer from β-irone.

The mixture has a strong fruity (raspberry) and flowery odour with a woody and a weak tobacco-like note.

EXAMPLE 3

Synthesis of 2,4,4-trimethyl-3-(2'-methylbut-2'-en-1'-yl)-cyclohex-2-en-1-one (cis and trans) and its (2'-methylbut-3'-en-1'-yl) isomer.

α-Isomethylionone was directly hydrogenated to dihydro-isomethylionol at 130° C. and 10 ato using 2% Nickel catalyst. The resulting compound was dehydrated in hexamethylphosphorous triamide and oxidized with tert.butylchromate as described in example 1 to yield a mixture of the title compounds, which could be separated gaschromatographically.

NMR spectral data:
(2'-methylbut-2'-en-1'-yl)-isomer (cis and trans): 1.0–1.2 (6H); 1.5–1.7 (6H); 2.8–3.2 (m, 2H); 4.9–5.4 (m, 1H).
(2'-methylbut-3'-en-1'-yl)-isomer: 0.9–1.2 (9H); 1.5–1.7 (3H); 4.8–6.1 (m, 3H).

The mixture has a fresh fruity and rose-like odour.

EXAMPLE 4

Synthesis of 2,4,4-trimethyl-3-butylcyclohexan-1-one.

The mixture of compounds obtained according to example 1 starting from β-ionone is dissolved in methanol and hydrogenated at atmospheric pressure and room tempertaure using 5% Palladium on charcoal as a catalyst.

NMR spectral data: 0.8–1.1 (m, 12H); 1.1–1.9 (m, 9H): 1.9–2.4 (m, 3H).

EXAMPLE 5

Synthesis of 2,4,4-trimethyl-3-(but-1-yl)-cyclohex-2-en-1-one.

18 g Of the mixture of alkenes obtained by dehydration of dihydro-β-ionol as described in example 1 was dissolved in 150 ml of methanol and hydrogenated at atmospheric pressure using 0.5 g of a catalyst consisting of 5% Palladium on charcoal. Hydrogenation was stopped when the uptake of hydrogen markedly slowed down. A 1:1 mixture of 1,3,3-trimethyl-2-(but-1-yl)-cyclohex-1-ene and 1,3,3-trimethyl-2-(but-1-yl)-cyclohexane was obtained. This mixture was oxidized with tert.butyl chromate as described in example 1, yielding a mixture of the title compound and 1,3,3-trimethyl-2-(but-1-yl)-cyclohexane. The mixture was fractionated yielding 6.75 g of the title compound boiling at 90°–92° C. (4 Torr).

The compound has a sweet fruity odour, with distinct woody, herbal and hay-like note.

EXAMPLE 6

Raspberry flavour concentrate

A standard raspberry flavour composition was prepared according to the following recipe:

| | |
|---|---|
| Ceraniol | 20 parts by weight |
| Vanillin | 50 parts by weight |
| Phenylethanol | 50 parts by weight |
| Maltol | 25 parts by weight |
| p,Hydroxybenzylacetone | 50 parts by weight |
| α-Ionone | 150 parts by weight |
| Benzyl acetate | 100 parts by weight |
| Isobutyl acetate | 100 parts by weight |
| Ethyl acetate | 150 parts by weight |
| Amyl acetate | 100 parts by weight |
| Orris root oil | 20 parts by weight |
| Hex-3-en-1-ol | 20 parts by weight |
| Anisyl acetate | 25 parts by weight |
| | 900 |

50 g of this standard flavour composition were diluted with 950 g of ethylalcohol to form a ready to use flavour concentrate.

Another ready to use flavour concentrate was prepared by adding 100 mg of the mixture of compounds obtained in example 1 to 1000 g of a flavour concentrate obtained as described above. Carbonated beverages were prepared from both flavour concentrates using 1 g of the flavour concentrate for each liter of finished beverage.

In a pair test a 12 person panel had a unanimous preferance for the beverage containing the compounds of the invention for having not only a stronger but also a more natural raspberry flavour.

EXAMPLE 7

Apple flavour composition

A standard apple flavour composition was prepared according to the following recipe:

| | |
|---|---|
| Isoeugenol | 4 parts by weight |
| Benzyl propionate | 4 parts by weight |
| Citronellyl formiate | 8 parts by weight |
| Citral | 8 parts by weight |
| γ-Undercalactone | 8 parts by weight |
| Hex-3-en-1-yl acetate | 15 parts by weight |
| Amyl formiate | 20 parts by weight |
| Ethyl heptanoate | 20 parts by weight |
| Acetaldehyde | 20 parts by weight |
| Amyl pentanoate | 100 parts by weight |
| Ethyl pentanoate | 40 parts by weight |
| Heptyl acetate | 40 parts by weight |
| 2-Methylbutanal | 50 parts by weight |
| Ethyl formiate | 80 parts by weight |
| Hex-3-en-1-yl formiate | 80 parts by weight |
| Hexyl acetate | 350 parts by weight |
| Ethyl acetate | 153 parts by weight |
| | 1000 |

75 g of this standard flavour composition was diluted with 925 g of ethylalcohol to form a ready to use flavour concentrate.

Another ready to use flavour concentrate was prepared by adding 1 g of the compound obtained according to example 3 to 1000 g of the flavour concentrate obtained as described above.

Carbonated beverages were prepared from both flavour concentrates using 1 g of the concentrate for each liter of finished beverage. In a triangle test 8 out of 10 persons had a clear preference for the beverage with the compound of the invention for having a more rounded off apple flavour.

EXAMPLE 8

An aftershave perfume concentrate was prepared according to the following recipe:

| | |
|---|---|
| Musk ambrette | 40 parts by weight |
| Musk ketone | 30 parts by weight |
| Benzoë resin Siam | 30 parts by weight |
| Mousse de chene absolute | 20 parts by weight |
| Coumarin | 10 parts by weight |
| Galbanum resin | 10 parts by weight |
| Patchouly oil | 250 parts by weight |
| Acetylcedrene | 150 parts by weight |
| α-Isomethylionone | 100 parts by weight |
| Bergamot oil | 100 parts by weight |
| Vetiveryl acetate | 50 parts by weight |
| 12-Oxahexadecanolide | 50 parts by weight |
| Phenylethanol | 30 parts by weight |
| Ylang ylang oil | 20 parts by weight |
| Castoreum resin[1] | 50 parts by weight |
| Amberoxide[2] | 10 parts by weight |
| Basil oil[2] | 10 parts by weight |
| Addition A | 40 parts by weight |
| | 1000 |

[1]10% solution in benzylalcohol
[2]10% solution in diethyl phthalate

The following solutions of compounds of the invention in diethylphthalate were successfully tried as "addition A":

10% mixture of compounds obtained in example 1
10% 2,4,4-trimethyl-3-(but-2'-en-1'-yl)-cyclohex-2-en-1-one (cis and trans mixture).
10% 2,4,4-trimethyl-3-(but-2'-en-1'-yl)-cyclohex-2-en-1-one
20% 2,4,4-trimethyl-3-(pent-3'-en-1'-yl)-cyclohex-2-en-1-one.

EXAMPLE 9

A creme perfume concentrate was prepared according to the following recipe:

| | |
|---|---|
| Benzoë resin Siam | 25 parts by weight |
| Musk R$_1$[1] | 20 parts by weight |
| Benzyl salicylate | 200 parts by weight |
| α-Hexyl-cinnamaldehyde | 100 parts by weight |
| Hydroxycitronellal | 100 parts by weight |
| α-Isomethylionone | 80 parts by weight |
| Citronellol | 70 parts by weight |
| Bergamot oil | 65 parts by weight |
| Benzyl acetate | 50 parts by weight |
| Phenylethanol | 50 parts by weight |
| Bois de rose oil | 40 parts by weight |
| Acetylcedrene | 40 parts by weight |
| Ylang ylang oil | 40 parts by weight |
| 3-Isocamfylcyclohexanol | 30 parts by weight |
| Vetiveryl acetate | 20 parts by weight |
| γ-Undecalactone | 5 parts by weight |
| Cardamon oil[2] | 20 parts by weight |
| Calamus oil [2] | 15 parts by weight |
| Product of example 1[2] | 130 parts by weight |
| | 1000 |

[1]Perfume compound of Naarden International N.V.
[2]10% solution in diethyl phthalate.

We claim:

1. In a process for preparing a flavoring composition containing carriers, diluents, essential oils and other auxiliary materials, the step of adding thereto an amount of at said composition, said ketone compound having the structural formula

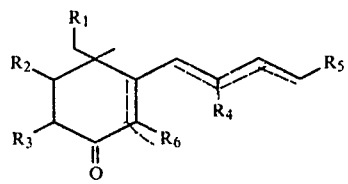

wherein groups $R_1$ to $R_5$ are the same or different and are hydrogen or methyl, and the dotted lines are possible sites for double bonds provided that the side chain carrying said groups $R_4$ and $R_5$ contains not more than one double bond, and $R_6$ is hydrogen, methyl or ethyl if the bond between $R_6$ and the nucleus of said compound is monovalent, or methylene or ethylidene if said bond is a double bond.

2. A process according to claim 1 wherein the compound added to said flavor composition is a cycloaliphatic saturated or unsaturated ketone wherein $R_1$ is hydrogen and only one of the groups $R_2$–$R_5$ is methyl, the remainder of said groups being hydrogen.

3. A process according to claim 2 wherein groups $R_2$–$R_5$ of said compound are all hydrogen.

4. A flavoring composition containing carriers, diluents, essential oils and other auxiliary materials further comprising an amount of at least one ketone compound effective for imparting a fruit-like flavor note to said composition, said ketone compound having the structural formula

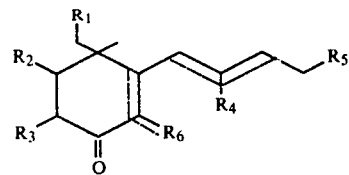

wherein groups $R_1$–$R_5$ are the same or different and are hydrogen or methyl, and the dotted lines are possible sites for double bonds provided that the side chain carrying said groups $R_4$ and $R_5$ contains not more than one double bond, and $R_6$ is hydrogen, methyl or ethyl if the bond between $R_6$ and the nucleus of said compound is monovalent, or methylene or ethylidene if said bond is a double bond.

5. A composition according to claim 4 wherein the ketone compound is a cycloaliphatic saturated or unsaturated ketone and wherein $R_1$ is hydrogen and only one of the groups $R_2$–$R_5$ is methyl, the remainder of said groups being hydrogen.

6. A composition according to claim 5 wherein groups $R_2$–$R_5$ of said compound are all hydrogen.

7. A flavored product selected from the group consisting of foodstuffs and beverages containing an amount of at least one ketone compound effective for imparting a fruit-like flavor note to said product, said compound having the structural formula wherein groups $R_1$ to $R_5$ are the same or different and are hydrogen or methyl, and the dotted lines are possible sites for double bonds provided that the side chain carrying said groups $R_4$ and $R_5$ contains not more than one double bond, and $R_6$ is hydrogen, methyl or ethyl if the bond between $R_6$ and the nucleus of said compound is monovalent, or methylene or ethylidene if said bond is a double bond.

8. A flavored product according to claim 7 wherein the amount of the ketone compound present therein is between about 0.005 to 100 ppm.

* * * * *

UNITED STATES PATENT AND TRADEMARK OFFICE
CERTIFICATE OF CORRECTION

PATENT NO. : 4,246,292
DATED : January 20, 1981
INVENTOR(S) : Könst et al.

It is certified that error appears in the above—identified patent and that said Letters Patent is hereby corrected as shown below:

Column 1, Line 38, "en-1-ene" should read --en-1-one--;

Column 1, Line 46, after "compounds" insert --of the--;

Column 1, Line 66, "Some variations" should begin a new paragraph;

Column 3, Line 39, before "18" delete "b";

Column 3, Line 50, after "and" insert --the--;

Column 4, Line 49, "temperture" should read --temperature--;

Column 5, Line 22, opposite "Hex-3-en-1-ol", "20 parts" should read --60 parts--;

Column 5, Line 51, "Undercalactone" should read --Undecalactone--;

UNITED STATES PATENT AND TRADEMARK OFFICE
CERTIFICATE OF CORRECTION

PATENT NO. : 4,246,292
DATED : January 20, 1981
INVENTOR(S) : Könst et al.

It is certified that error appears in the above—identified patent and that said Letters Patent is hereby corrected as shown below:

Column 6, Line 39, "(but-2'-en-1'-yl)" should read --(but-3'-en-1'-yl)--;

Column 6, Line 63, "130" should read --30--;

Column 7, Line 6, after "of at" insert --least one ketone compound effective for imparting a fruit-like flavor note to--;

Column 8, Claim 4,

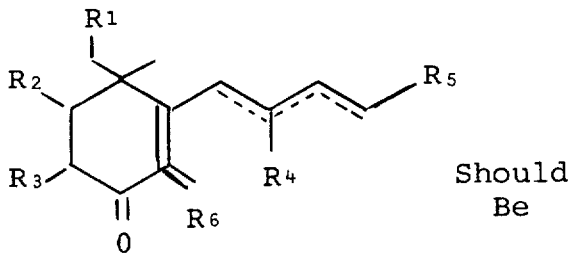 Should Be 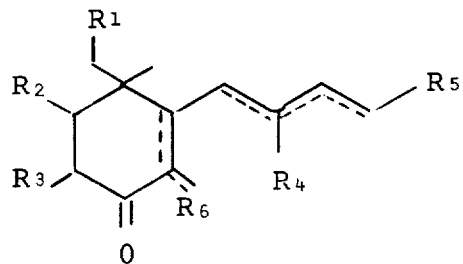

UNITED STATES PATENT AND TRADEMARK OFFICE
CERTIFICATE OF CORRECTION

PATENT NO. : 4,246,292
DATED : January 20, 1981
INVENTOR(S) : Könst et al.

It is certified that error appears in the above—identified patent and that said Letters Patent is hereby corrected as shown below:

Column 8, Claim 7,

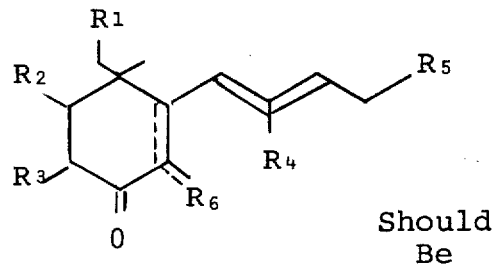  Should Be  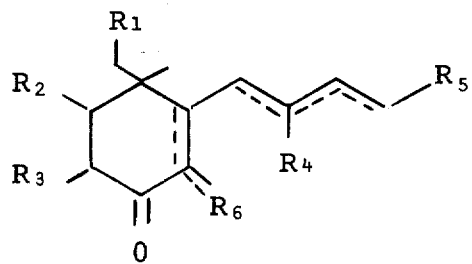

Signed and Sealed this

Twenty-sixth Day of May 1981

[SEAL]

Attest:

RENE D. TEGTMEYER

Attesting Officer　Acting Commissioner of Patents and Trademarks